(12) United States Patent
Schader et al.

(10) Patent No.: US 11,484,663 B2
(45) Date of Patent: Nov. 1, 2022

(54) DRUG DELIVERY DEVICE

(71) Applicant: SANOFI, Paris (FR)

(72) Inventors: Marc Schader, Frankfurt am Main (DE); William Timmis, Melbourn (GB); Thomas Mark Kemp, Melbourn (GB); Jim Bradford, Melbourn (GB)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 16/760,642

(22) PCT Filed: Nov. 1, 2018

(86) PCT No.: PCT/EP2018/079937
§ 371 (c)(1),
(2) Date: Apr. 30, 2020

(87) PCT Pub. No.: WO2019/086575
PCT Pub. Date: May 9, 2019

(65) Prior Publication Data
US 2020/0345948 A1 Nov. 5, 2020

(30) Foreign Application Priority Data
Nov. 3, 2017 (EP) .................................... 17306521

(51) Int. Cl.
*A61M 5/32* (2006.01)
(52) U.S. Cl.
CPC ........ *A61M 5/3213* (2013.01); *A61M 5/3204* (2013.01)

(58) Field of Classification Search
CPC .............. A61M 5/3213; A61M 5/3204; A61M 2005/3247; A61M 2205/273; A61M 5/50; A61M 5/3202
See application file for complete search history.

(56) References Cited

U.S. PATENT DOCUMENTS

2003/0199822 A1 10/2003 Alchas et al.
2008/0228147 A1 9/2008 David-Hegerich et al.
2016/0120751 A1* 5/2016 Mounce ................. A61P 19/10
604/189
(Continued)

FOREIGN PATENT DOCUMENTS

CN 101264360 9/2008
EP 1970086 9/2008
(Continued)

OTHER PUBLICATIONS

PCT International Preliminary Report on Patentability in Appln. No. PCT/EP2018/079937, dated May 5, 2020, 8 pages.
(Continued)

*Primary Examiner* — Theodore J Stigell
*Assistant Examiner* — Rachel T. Smith
(74) *Attorney, Agent, or Firm* — Fish & Richardson P.C.

(57) ABSTRACT

The disclosure relates to a drug delivery device including: a housing configured to contain a drug container with a needle, a needle shroud that is telescopically connected to the housing, and a cap that is configured to be releasably connected to the housing before use of the device. At least one of the cap and the needle shroud is adapted to unreleasably lock the cap onto the housing after reapplying the cap onto the housing after the drug delivery device is used.

14 Claims, 10 Drawing Sheets

(56) References Cited

U.S. PATENT DOCUMENTS

2016/0325044 A1* 11/2016 Tschirren ............ A61M 5/3202
2019/0151561 A1*  5/2019 Bernhard ............ A61M 5/3213

FOREIGN PATENT DOCUMENTS

| EP | 2201975 | 6/2010 | | |
|----|---------|--------|---|---|
| WO | WO 2011/092518 | 8/2011 | | |
| WO | WO 2012/073040 | 6/2012 | | |
| WO | WO 2016/193352 | 12/2016 | | |
| WO | WO 2017/059455 | 4/2017 | | |
| WO | WO-2017059455 A1 * | 4/2017 | .......... | A61M 5/3202 |

OTHER PUBLICATIONS

PCT International Search Report and Written Opinion in Appln. No. PCT/EP2018/079937, dated Dec. 13, 2018, 12 pages.

* cited by examiner

DRUG DELIVERY DEVICE

CROSS REFERENCE TO RELATED APPLICATIONS

The present application is the national stage entry of International Patent Application No. PCT/EP2018/079937, filed on Nov. 1, 2018, and claims priority to Application No. EP 17306521.0, filed on Nov. 3, 2017, the disclosures of which are incorporated herein by reference.

TECHNICAL FIELD

The disclosure generally relates to a drug delivery device. In particular, the disclosure relates to a drug delivery device that is adapted to unreleasably lock a cap onto the housing after reapplying the cap onto the housing after the drug delivery device is used.

BACKGROUND

A drug delivery device may completely or partially replace activities involved in parenteral drug delivery from a manual device. Typically, such activities include removal of a protective needle cap, insertion of the needle, providing the force for administering the injection and possibly removal and shielding of the used needle. The shielding of a used needle may be achieved by a needle shroud coupled to a lock mechanism for a needle safety shroud lock before and after the injection.

There remains a need for an improved drug delivery device.

SUMMARY

According to the present disclosure, a drug delivery device comprises at least a housing adapted to contain a drug container with a needle, a needle shroud that is telescopically arranged with the housing, and a cap that is configured to be releasably connected to the housing before use of the device. At least one of the cap and the needle shroud is/are adapted to non-releasably lock the cap to the housing after reapplying the cap onto the housing after use of the device, e.g. after an injection.

Such a drug delivery device ensures retention of a post-use shroud lock in the event of recapping. The post-use shroud locks the needle shroud against proximal movement after use of the device. Recapping after use of the drug delivery device may cause a deflection to a shroud beam of the needle shroud that enables engaging the post-use shroud lock. If a cap is left in place for a prolonged period, and/or under elevated temperature, the shroud beam can be susceptible to creep. Creep reduces the stress within the shroud beam such that when the cap is removed, the shroud beam does not return to its original form and the overlap with a shroud lock boss within the housing. Locking the cap unreleasably onto the housing after use of the device will provide needle safety.

In an exemplary embodiment, the needle shroud comprises a shroud beam that is biased radially outwards from a shroud body. The shroud beam has a locking tab protruding outwards and a shroud ramp that is distally spaced from the locking tab, wherein a recess is formed between the shroud ramp and the locking tab and wherein the recess is adapted to receive a proximal cap end after reapplying the cap onto the housing after use of the device. The shroud ramp increases in a proximal direction, thereby forming a proximal stop that may not be overcome by the proximal cap end if it is received within the recess formed between the shroud ramp and the locking tab. The cap is thus fixed to the needle shroud and is not allowed to be removed again.

Furthermore, the cap may comprise a cut-out that is arranged proximally behind the proximal cap end and wherein the cut-out is adapted to receive the shroud ramp when the proximal cap end is received within the recess after reapplying the cap onto the housing after use of the device. The cut-out ensures receiving the proximal cap end into the recess.

According to another aspect of the present disclosure, a drug delivery device comprises at least a housing adapted to contain a drug container with a needle, a needle shroud that is telescopically arranged with the housing and a cap that is configured to be releasably connected to the housing before use of the device. At least one of the cap and the needle shroud is/are adapted to at least partially prevent the cap from being reapplied onto the housing after use of the device.

Such a drug delivery device ensures retention of a post-use shroud lock in the event of recapping as well. Due to the prevention of recapping itself, the post-use shroud lock cannot be released after use of the device. This will provide needle safety.

In an exemplary embodiment, the needle shroud comprises a shroud beam that is biased radially outwards from a shroud body, wherein the shroud beam has a locking tab protruding outwards and wherein the locking tab comprises a distal steep edge. The steep edge is configured as a distal stop for a proximal cap end when the cap is reapplied onto the housing after use of the device. In particular, the steep edge requires an increased assembly force to engage the post-use shroud lock compared with an assembly of conventional drug delivery devices. If the cap is reapplied on the housing, the force required to overcome and release the post-use shroud lock may be too high. Thus, a user may be prevented from fully inserting the cap back into the device.

In another exemplary embodiment, the cap comprises a grasper having at least one pair of flexible grasper arms that are arranged on a grasper body biased outwards, wherein each of the grasper arms projects through a gap arranged within the cap and flex outwards during cap removal. The outward flexed grasper arms prevent the device from being recapped, because the grasper arms abut against a distal end of the needle shroud when reapplying the cap onto the housing. The flexible grasper arms can be deflected inwards during assembly by an assembling tool via the gaps in the cap.

In a further exemplary embodiment, the cap comprises at least one pair of flexible cap arms that are arranged on an inner circumference of the cap biased outwards, wherein each of the cap arms projects through a gap arranged within the cap and flex outwards during cap removal. In particular, the flexible cap arms are arranged on an inner cap tube. While removing the cap from the device, the flexible cap arms are allowed to flex outwards. The cap arms flex outwards in order to prevent the device from being recapped, because the cap arms abut against the distal end of the needle shroud when reapplying the cap onto the housing.

Furthermore, the grasper may comprise a number of slots. The slots increase a clearance for the cap arms once they are deflected. This prevents an increase of a cap removal force, because the cap arms do not join the grasper. Instead of the slots, a length of the cap arms may be increased.

Moreover, the needle shroud may comprise a number of inner ribs projecting radially inwards. The inner ribs maybe arranged on a distal end of the needle shroud and are provided to prevent a shroud spring from joining the cap arms. In particular, the inner ribs offset the shroud spring from the distal end of the needle shroud.

In an exemplary embodiment, the needle shroud further comprises a number of shroud gaps which are configured to receive the cap arms before final assembly, in particular in a control-subassembly state. This prevents relaxation of the cap arms due to creep during storage. According to a further aspect of the present disclosure, a drug delivery device comprises at least a housing adapted to contain a drug container with a needle, a needle shroud that is telescopically arranged with the housing and a cap that is configured to be releasably connected to the housing before use of the device. At least one of the cap and the needle shroud is/are adapted to allow a reapplying of the cap onto the housing after use of the device without the cap being allowed to release a post-use shroud.

Such a drug delivery device ensures retention of the post-use shroud lock in the event of recapping as well. Preventing the cap from releasing the post-use shroud lock after reapplying the cap onto the housing after use of the device will provide needle safety.

In an exemplary embodiment, the needle shroud comprises a shroud beam that is biased radially outwards from a shroud body, wherein the shroud beam has a locking tab protruding outwards. The post-use shroud lock comprises the locking tab that abuts a housing ramp proximally when the post-use shroud lock is engaged. The cap is sized such that a proximal cap end is distally spaced from the locking tab when the cap is in place before use of the device and after reapplying the cap onto the housing after use of the device. Due to the short length of the cap, the cap may be removed and replaced as many times by the user with no effect on the post-use shroud lock. For disengaging the post-use shroud lock in final assembly, the cap may be removed during final assembly in order to provide space for inserting an assembly tool.

To prevent the post-use shroud lock from engaging before final assembly, the needle shroud is held in position during assembly of the device by a projection that is arranged proximally on the needle shroud and that protrudes inwards. The projection abuts distally a stop formed on a locking pin of a syringe carrier.

Moreover, the drug delivery device comprises a pre-use shroud lock configured to lock a position of the needle shroud relative to the housing of the drug delivery device before use of the device. The pre-use shroud lock prevents depression of the needle shroud when the cap is in place. In particular, it prevents the device from activating unintentionally when upon dropped. Furthermore, the cartridge or container is prefilled with a drug, e.g. an allergic drug or a diabetic drug. The cartridge or container may also be prefilled with biologics. The drug delivery device is for instance an auto-injector, a pen-injector or a syringe.

The drug delivery device, as described herein, may be configured to inject a drug or medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector.

The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 5 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may be activated via an activation mechanism. Such an activation mechanism can include one or more of a button, a lever, a needle shroud, or other activation component. Activation may be a one-step or multi-step process. That is, a user may need to activate one or more activation mechanism in order to cause the automated function. For example, a user may depress a needle shroud against their body in order to cause injection of a medicament. In other devices, a user may be required to depress a button and retract a needle shield in order to cause injection.

In addition, such activation may activate one or more mechanisms. For example, an activation sequence may activate at least two of needle insertion, medicament injection, and needle retraction. Some devices may also require a specific sequence of steps to cause the one or more automated functions to occur. Other devices may operate with sequence independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Further scope of applicability of the present disclosure will become apparent from the detailed description given hereinafter. However, it can be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE FIGURES

The present disclosure will become more fully understood from the detailed description given below and the accompanying drawings, which are given by way of illustration only, and do not limit the present disclosure, and wherein.

Corresponding parts are marked with the same reference symbols in all figures.

DETAILED DESCRIPTION

Figure 1A:
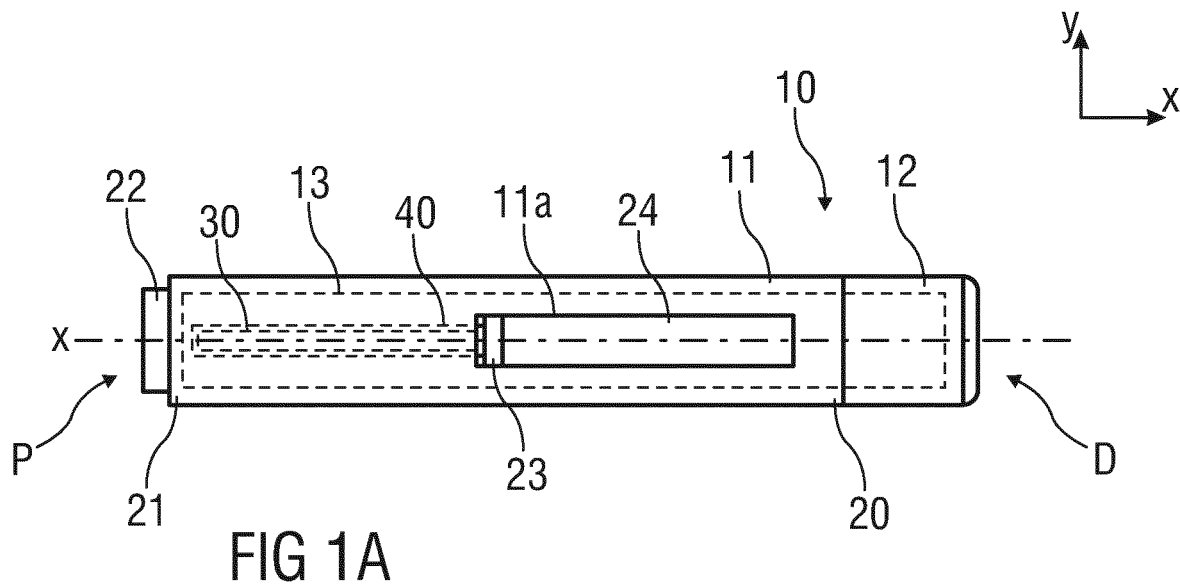
FIGS. 1A to 1B are schematic views of a drug delivery device.
Figure 1B:
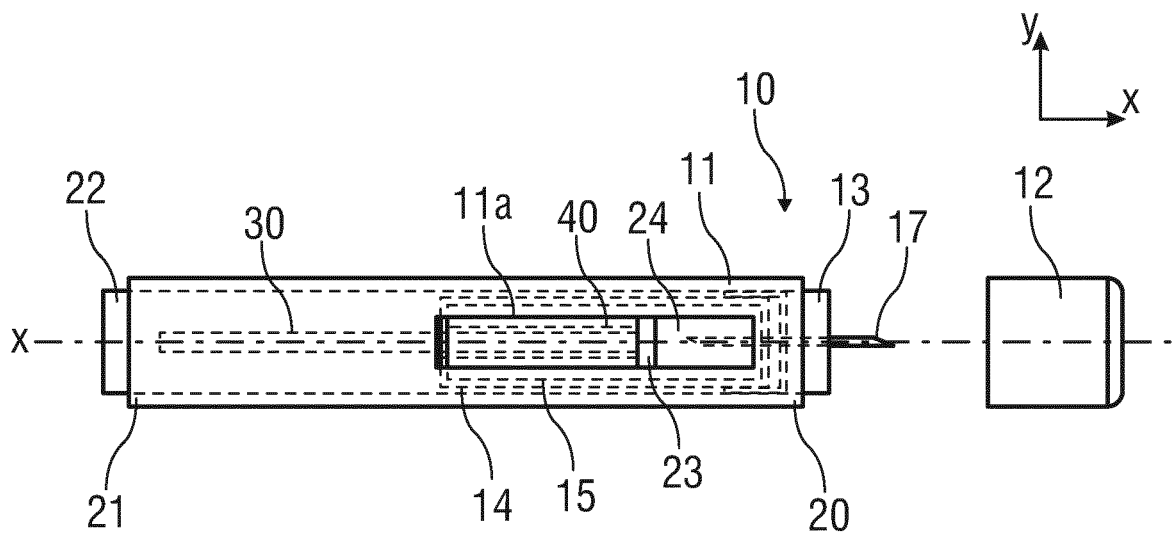

According to some embodiments of the present disclosure, an exemplary drug delivery device 10 is shown in FIGS. 1A and 1B.

Device 10, as described above, is configured to inject a drug or medicament into a patient's body.

Device 10 includes a housing 11 which typically contains a reservoir containing the medicament to be injected (e.g., a syringe 24 or a container) and the components required to facilitate one or more steps of the delivery process.

Device 10 can also include a cap assembly 12 that can be detachably mounted to the housing 11, in particular on a distal or front end D of the device 10. Typically, a user must remove cap assembly or cap 12 from housing 11 before device 10 can be operated. The cap 12 may further include a grasper 12.1 (shown in FIG. 11) arranged to engage and grip the needle shroud 13. The grasper 12.1 forms an inner grip element and is fixed to the cap 12.

As shown, housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

Device 10 can also include a needle shroud 13 coupled to the housing 11 to permit movement of the shroud 13 relative to the housing 11. For example, the shroud 13 can move in a longitudinal direction parallel to longitudinal axis X. Specifically, movement of the shroud 13 in a proximal direction can permit a needle 17 to extend from distal region 20 of housing 11. Insertion of the needle 17 can occur via several mechanisms. For example, the needle 17 may be fixedly located relative to housing 11 and initially be located within an extended needle shroud 13. Proximal movement of the shroud 13 by placing a distal end of shroud 13 against a patient's body and moving housing 11 in a distal direction will uncover the distal end of needle 17. Such relative movement allows the distal end of needle 17 to extend into the patient's body. Such insertion is termed "manual" insertion as the needle 17 is manually inserted via the patient's manual movement of the housing 11 relative to the shroud 13.

Another form of insertion is "automated," whereby the needle 17 moves relative to housing 11. Such insertion can be triggered by movement of shroud 13 or by another form of activation, such as, for example, a button 22. As shown in FIGS. 1A & 1B, button 22 is located at a proximal or back end P of the housing 11. However, in other embodiments, button 22 could be located on a side of housing 11. In further embodiments, the button 22 has been deleted and is replaced for instance by a shroud trigger mechanism, e.g. provided by pushing the needle shroud 13 inside the housing when the drug delivery device is put onto an injection side.

Other manual or automated features can include drug injection or needle retraction, or both. Injection is the process by which a bung or piston 23 is moved from a proximal location within a container or syringe 24 to a more distal location within the syringe 24 in order to force a medicament from the syringe 24 through needle 17.

In some embodiments, an energy source, e.g. a drive spring 30 is arranged in a plunger 40 and is under compression before device 10 is activated. A proximal end of the drive spring 30 can be fixed within proximal region 21 of housing 11, and a distal end of the drive spring 30 can be configured to apply a compressive force to a proximal surface of piston 23. Following activation, at least part of the energy stored in the drive spring 30 can be applied to the proximal surface of piston 23. This compressive force can act on piston 23 to move it in a distal direction. Such distal movement acts to compress the liquid medicament within the syringe 24, forcing it out of needle 17.

Following injection, the needle 17 can be retracted within shroud 13 or housing 11. Retraction can occur when shroud 13 moves distally as a user removes device 10 from a patient's body. This can occur as needle 17 remains fixedly located relative to housing 11. Once a distal end of the shroud 13 has moved past a distal end of the needle 17, and the needle 17 is covered, the shroud 13 can be locked. Such locking can include locking any proximal movement of the shroud 13 relative to the housing 11.

Another form of needle retraction can occur if the needle 17 is moved relative to the housing 11. Such movement can occur if the syringe within the housing 11 is moved in a proximal direction relative to the housing 11. This proximal movement can be achieved by using a retraction spring (not shown), located in the distal region 20. A compressed retraction spring, when activated, can supply sufficient force to the syringe 24 to move it in a proximal direction. Following sufficient retraction, any relative movement between the needle 17 and the housing 11 can be locked with a locking mechanism. In addition, button 22 or other components of device 10 can be locked as required.

In some embodiments, the housing may comprise a window 11a through which the syringe 24 can be monitored.

Figure 2:
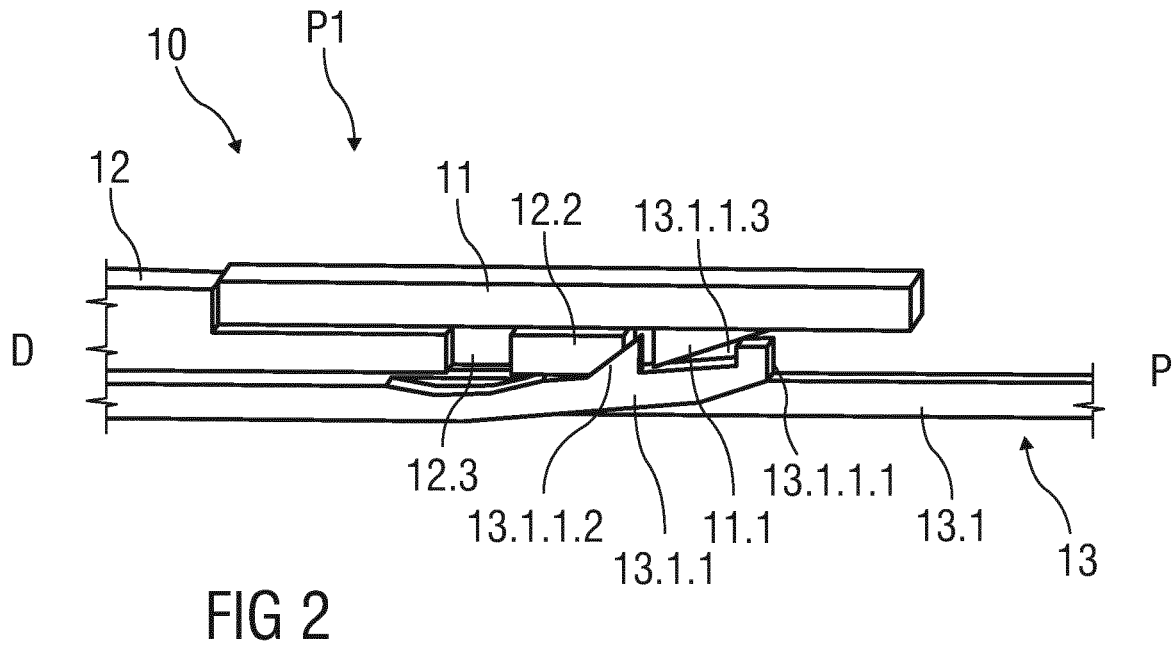
FIG. 2 is a schematic perspective view of separate components of a first exemplary embodiment of a drug delivery device in a pre-use state.
Figure 3:
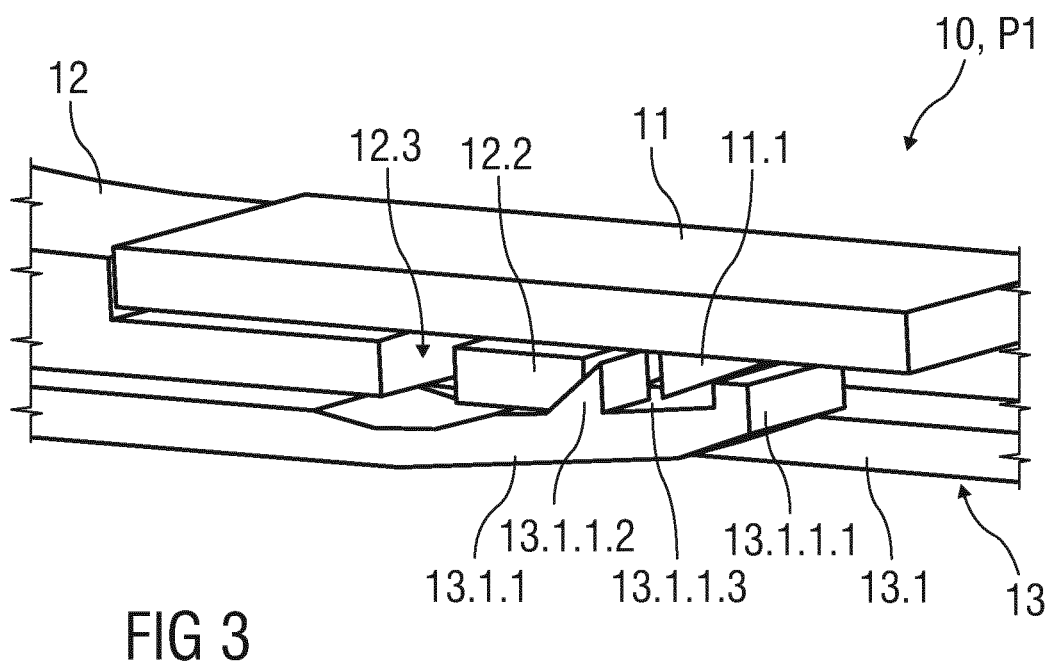
FIG. 3 is an enlarged perspective view of the first exemplary embodiment of the drug delivery device in the pre-use state.

FIG. 2 shows a perspective view of separate components of a first exemplary embodiment of a drug delivery device 10 in a pre-use state P1. FIG. 3 shows an enlarged perspective view of the first exemplary embodiment of the drug delivery device 10 in the pre-use state P1. In particular, a part of the needle shroud 13, a shroud beam 13.1.1, a proximal cap end 12.2 and a part of the housing 11 are shown.

Figure 4:
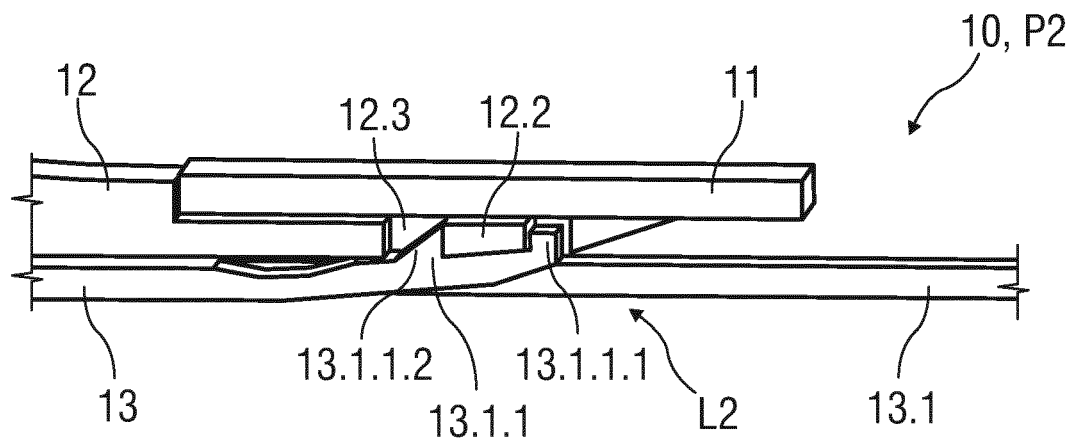
FIG. 4 is a schematic perspective view of the separate components of the drug delivery device in a post-use state according to the first exemplary embodiment.

The housing 11 comprises a housing ramp 11.1 that decreases in the proximal direction and that forms a stop on a distal side for a post-use shroud lock L2 (see FIG. 4). The needle shroud 13 comprises a shroud body 13.1 having the shroud beam 13.1.1 that is arranged on the shroud body 13.1 and biased radially outwards. The needle shroud 13 may have two or more shroud beams 13.1.1 (not shown). For example, several shroud beams 13.1.1 are symmetrically distributed around the entire circumference of the needle shroud 13.

The shroud beam 13.1.1 has a locking tab 13.1.1.1 protruding outwards and a shroud ramp 13.1.1.2 that is distally spaced from the locking tab 13.1.1.1 in a longitudinal direction of the shroud beam 13.1.1. Thus, a recess 13.1.1.3 is formed between the shroud ramp 13.1.1.2 and the locking tab 13.1.1.1. The recess 13.1.1.3 receives the housing ramp 11.1 of the housing 11 in the pre-use state P1 of the drug delivery device 10. A proximal cap end 12.2 abuts the shroud ramp 13.1.1.2 distally in the pre-use state P1. The cap 12 further comprises a cut-out 12.3 that is inserted in an inner circumference of the cap 12 distally behind the proximal cap end 12.2. In the pre-use state P1, the needle shroud 13 is in an extended position. In this extended position, the needle shroud 13 extends beyond the needle 17 and is locked in an axial position relative to the housing 11 by a pre-use shroud lock L1 (shown in FIG. 15). Thus, a risk of needle-stick injury is reduced.

For improving flexibility of assembly of the drug delivery device 10, it may be divided in two subassemblies, a control-subassembly 10.1 (shown exemplary in FIG. 14) and a drive-subassembly (not shown). The control-subassembly 10.1 comprises all parts and mechanisms which control access to the needle 17. In particular, the control-subassembly 10.1 comprises the cap 12, the needle shroud 13, the shroud spring 13.2 and the distal region 20 of the housing 11. In order to assemble the control-subassembly 10.1, the shroud spring 13.2 is inserted into the needle shroud 13 and the needle shroud 13 with the shroud spring 13.2 is inserted into the distal region 20 of the housing 11. The cap 12 is arranged over a distal end of the needle shroud 13 causing the shroud beam 13.1.1 to deflect so that it no longer interferes with the housing ramp 11.1 and the needle shroud 13 is allowed to move proximally. This requires a certain assembly force. After overcoming the housing ramp 11.1, the shroud beam 13.1.1 relaxes and the locking tab 13.1.1.1 is arranged proximally behind the housing ramp 11.1 as shown in FIG. 2, thereby holding the needle shroud 13 in position by the plunger 40 (not shown). The drive subassembly comprises the components required to deliver the drug and will be not explained in more detail.

For use of the drug delivery device 10, the cap 12 is removed by pulling it off and thus moving the cap 12 in the distal direction with respect to the needle shroud 13. The needle shroud 13 may be held in a retracted position by coupling to the plunger 40 and/or by coupling to another component of the drug delivery device 10. After using the drug delivery device 10, the needle shroud 13 limitedly moves in the distal direction until the shroud beam 13.1.1 flexes outwards and abuts the stop distally formed on the housing ramp 11.1 of the housing 11 so that the needle shroud 13 is locked relative to the housing 11 (shown in FIG. 4). In particular, the needle shroud 13 is coupled to a shroud spring 13.2 (shown in FIG. 11) for biasing the needle shroud 13 in the distal direction. The ends of the shroud spring 13.2 may directly act on a distal front end of the needle shroud 13 and a distal front side of the housing 11.

If the cap 12 is replaced on the drug delivery device 10 after use of it, the proximal cap end 12.2 moves proximally with respect to the needle shroud 13. While replacing the cap 12 onto the drug delivery device 10, the proximal cap end 12.2 passes the shroud ramp 13.1.1.2, which increases in the proximal direction, until it is received within the recess 13.1.1.3. The arrangement of the proximal cap end 12.2 in the recess 13.1.1.3 is possible due to the cut-out 12.3 that receives the shroud ramp 13.1.1.2 in the post-use state P2.

Figure 5:
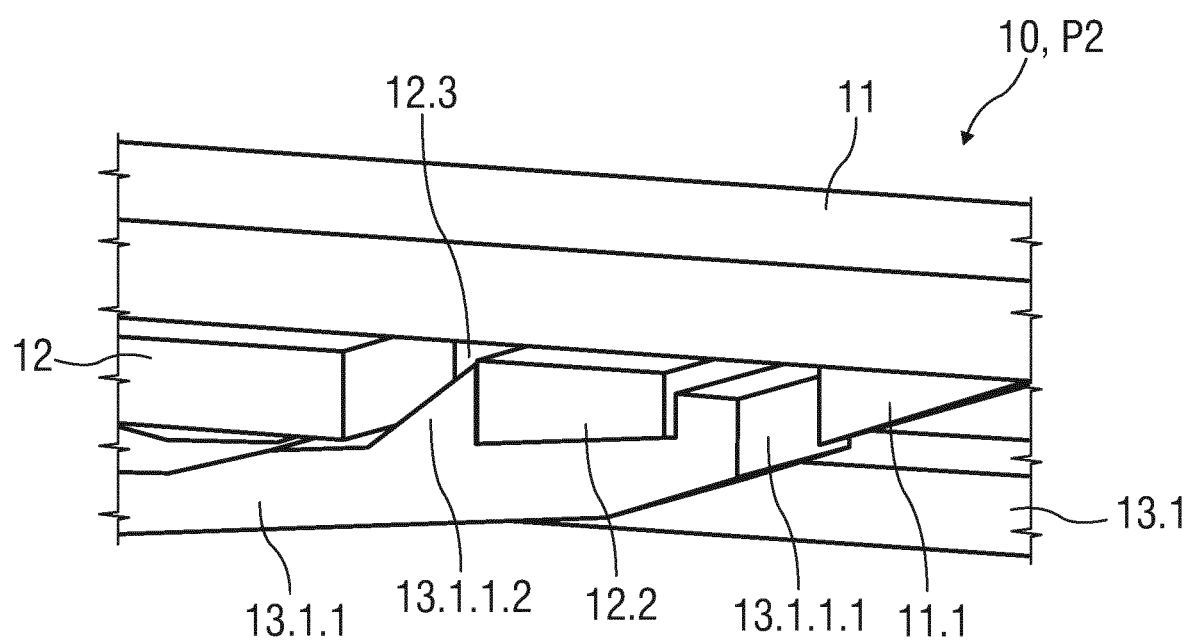
FIG. 5 is an enlarged perspective view of the first exemplary embodiment of the drug delivery device in the post-use state.

FIG. 4 shows the components of the drug delivery device 10 according to the first exemplary embodiment shown in FIG. 2 in the post-use state P2. FIG. 5 shows an enlarged perspective view of the components of the drug delivery device 10 according to the first exemplary embodiment shown in FIG. 2 in the post-use state P2.

The cap 12 is unreleasably locked to the drug delivery device 10 due to the arrangement of the proximal cap end 12.2 in the recess 13.1.1.3 and the shroud ramp 13.1.1.2 in the cut-out 12.3. Retention of the post-use shroud lock L2 in the event of recapping is thus ensured. Recapping after use of the drug delivery device 10 may cause a deflection to the shroud beam 13.1.1. If the cap 12 is left in place for a prolonged period, and/or under elevated temperature, the shroud beam 13.1.1 can be susceptible to creep. Creep reduces the stress within the shroud beam 13.1.1 such that when the cap 12 is removed, the shroud beam 13.1.1 does not return to its original form and the overlap with a shroud lock boss within the housing 1.1. Locking the cap 12 unreleasably onto the drug delivery device 10 in the post-use state P2 as shown in FIGS. 4 and 5 will provide needle safety.

Figure 6:
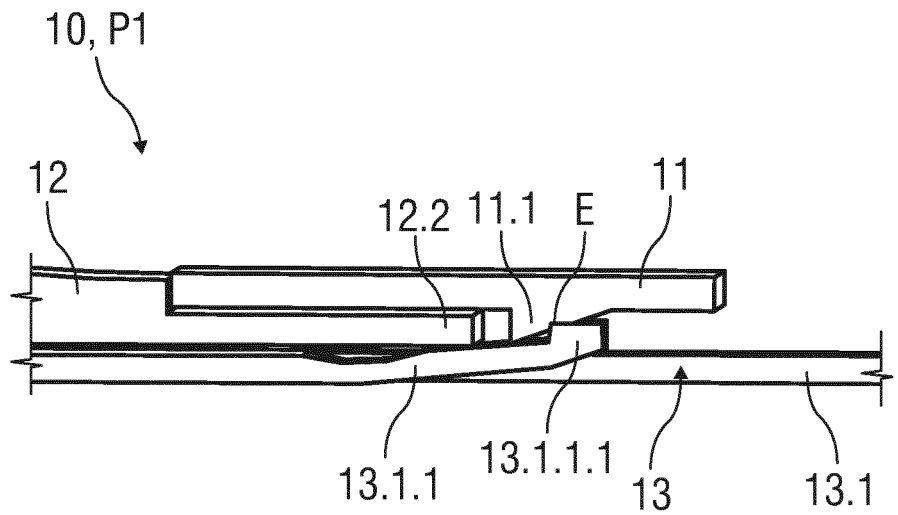
FIG. 6 is a schematic perspective view of separate components of a second exemplary embodiment of a drug delivery device in a pre-use state.
Figure 7:
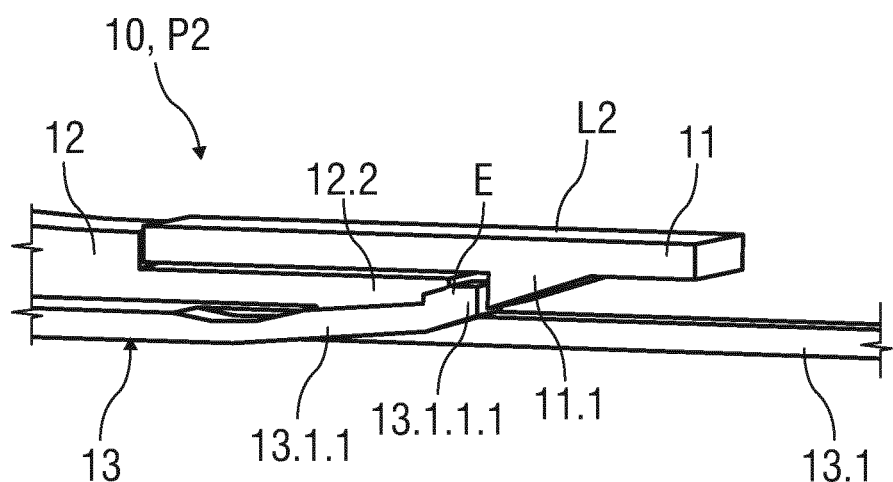
FIG. 7 is a schematic perspective view of the separate components of the drug delivery device in a post-use state according to the second exemplary embodiment.

FIG. 6 shows a schematic perspective view of the components of a second exemplary embodiment of a drug delivery device 10 in the pre-use state P1. FIG. 7 shows a schematic perspective view of the separate components of the second exemplary embodiment of the drug delivery device 10 in the post-use state P2. In particular, a part of the needle shroud 13, the shroud beam 13.1.1, the proximal cap end 12.2 and a part of the housing 11 are shown. The components of the drug delivery device 10 modified with respect to the first exemplary embodiment are the needle shroud 13, the shroud beam 13.1.1 and the cap 12.

The housing 11 is configured similar to the first exemplary embodiment of the drug delivery device 10 as shown in FIGS. 2 to 5. The shroud beam 13.1.1 comprises a locking tab 13.1.1.1 protruding outwards nearly similar to the locking tab 13.1.1.1 of the first exemplary embodiment of the drug delivery device 10 but with the difference that the locking tab 13.1.1.1 is configured with a steep edge E that requires an increased assembly force to engage the post-use shroud lock L2 compared with the drug delivery device 10 according to the first embodiment. In further contrast to the first embodiment of the drug delivery device 10, the shroud beam 13.1.1 has no shroud ramp 13.1.1.2 and the cap 12 has no cut-out 12.3.

In the pre-use state P1, the housing ramp 11.1 of the housing 11 abuts the locking tab 13.1.1 distally. Thus, the locking tab 13.1.1 is arranged proximally behind the housing ramp 11.1. After using the drug delivery device 10, the needle shroud 13 limitedly moves in the distal direction until the shroud beam 13 1.1 flexes outwards and abuts the stop distally formed on the housing ramp 11.1 of the housing 11. Thus, the locking tab 13.1.1 is arranged distally behind the housing ramp 11.1 so that the needle shroud 13 is locked relative to the housing 11 (shown in FIG. 7).

If the cap 12 is replaced onto the drug delivery device 10 after use of it, a proximal cap end 12.2 moves proximally with respect to the needle shroud 13 until the proximal cap end 12.2 abuts the locking tab 13.1.1. The force required to overcome the post-use shroud lock L2 may be too high. Thus, a user may be prevented from fully inserting the cap 12 back into the drug delivery device 10.

Figure 8:
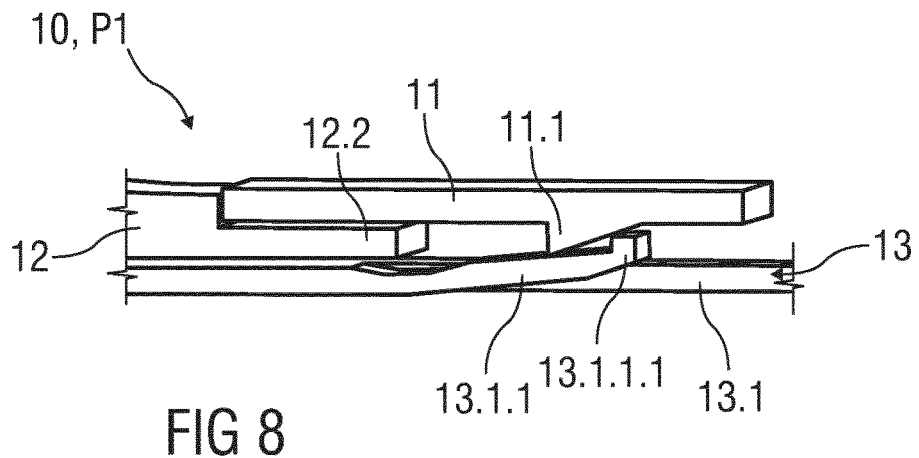
FIG. 8 is a schematic perspective view of separate components of a third exemplary embodiment of a drug delivery device in a pre-use state.
Figure 9:
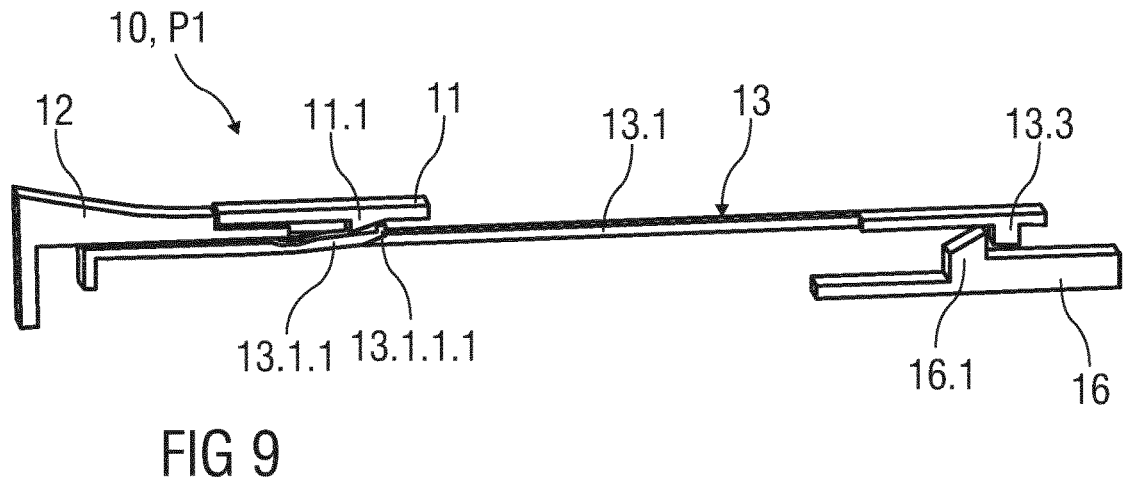
FIG. 9 is a further schematic perspective view of the separate components of the drug delivery device in a pre-use state according to the third exemplary embodiment.
Figure 10:
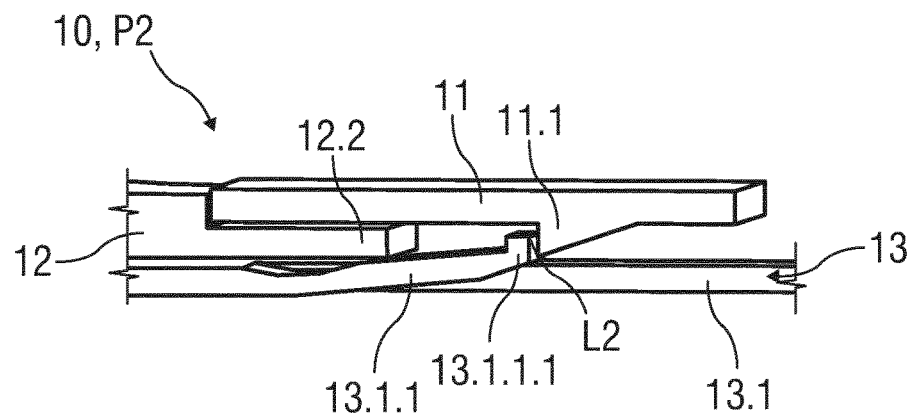
FIG. 10 is a schematic perspective view of the separate components of the drug delivery device in a post-use state according to the third exemplary embodiment.

FIG. 8 shows a schematic perspective view of separate components of a third exemplary embodiment of a drug delivery device 10 in the pre-use state P1. FIG. 9 shows a further schematic perspective view of the separate components of the third exemplary embodiment of the drug delivery device 10 in the pre-use state 10. FIG. 10 shows a schematic perspective view of the separate components of the third exemplary embodiment of the drug delivery device 10 in the post-use state P2. In particular, a part of the needle shroud 13, the shroud beam 13.1.1, the proximal cap end 12.2 and the housing 11 are shown. The components of the drug delivery device 10 modified with respect to the other exemplary embodiments are the needle shroud 13, the shroud beam 13.1.1, the cap 12 and the housing 11.

The shroud beam 13.1.1 comprises the locking tab 13.1.1.1 protruding outwards nearly similar to the locking tab 13.1.1.1 of the first exemplary embodiment of the drug delivery device 10 but with the difference that the shroud beam 13.1.1 has no shroud ramp 13.1.1.2.

In further contrast to the first embodiment of the drug delivery device 10, the proximal cap end 12.2 is shortened compared to the proximal cap end 12.2 of the cap 12 according to the first exemplary embodiment of the drug delivery device 10. In particular, the proximal cap end 12.2 is arranged distally spaced from the housing ramp 11.1 when the cap 12 is placed onto the drug delivery device 10 in the pre-use state P1. Thus, the proximal cap end 12.2 cannot engage the shroud beam 13.1.1 during final assembly in order to deflect the shroud beam 13.1.1 such that the shroud beam 13.1.1 is allowed to pass the housing ramp 11.1 and will be arranged proximally behind the housing ramp 11.1 as shown in FIG. 8. This may be solved by removing the cap 12 during final assembly and inserting an assembly tool by which the shroud beam 13.1.1 can be deflected. Alternatively or additionally, the needle shroud 13 may be interlocked to the housing 11 during assembly of the control sub-assembly 10.1 as shown in FIG. 9.

Here, the drug delivery device 10 additionally comprises a syringe carrier 16 having a locking pin 16.1 that is arranged distally on the syringe carrier 16 and protrudes radially outwards. The locking pin 16.1 distally engages a projection 13.3 arranged on the shroud body 13.1. In particular, the projection 13.3 protrudes inwards and is proximally spaced from the shroud beam 13.1.1. To prevent the after-use shroud lock L2 from engaging before final assembly, the projection 13.3 is arranged distally behind the locking pin 16.1.

After using the drug delivery device 10, the needle shroud 13 limitedly moves in the distal direction until the shroud beam 13.1.1 flexes outwards and abuts the stop distally formed on the housing ramp 11.1 of the housing 11. Thus, the locking tab 13.1.1 is arranged distally behind the housing ramp 11.1 so that the needle shroud 13 is locked relative to the housing 11 (shown in FIG. 10). If the cap 12 is replaced onto the drug delivery device 10 after use of it (shown in FIG. 10), the proximal cap end 12.2 moves proximally with respect to the needle shroud 13 until it reaches an end position, i. e. the cap 12 is fully replaced onto the drug delivery device 10. In this end position, the proximal cap end 12.2 does not abut the locking tab 13.1.1 but is distally spaced from the locking tab 13.1.1. Thus, a user may be replacing and removing the cap 12 as many as often as needed without any effect on the post-use shroud lock L2.

Figure 11:
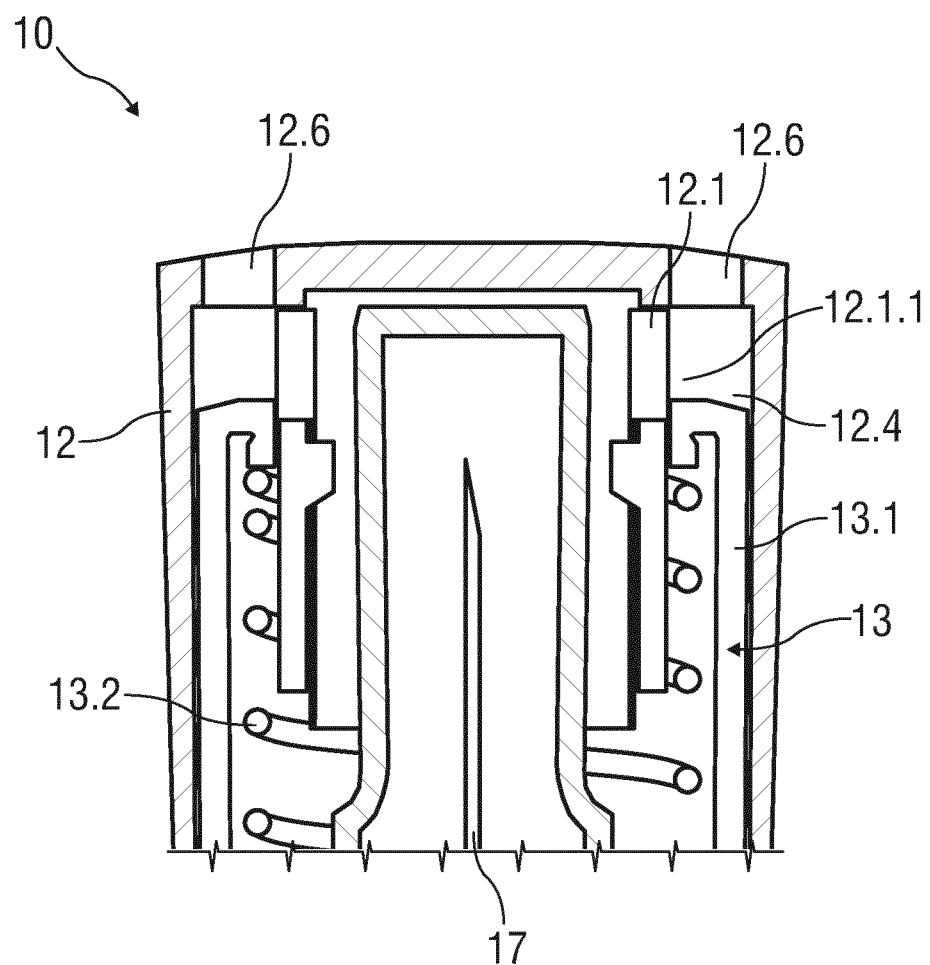
FIG. 11 is a sectional view of a longitudinal section of a distal end of a fourth exemplary embodiment of a drug delivery device.

FIG. 11 shows a sectional view of a longitudinal section of a distal region of a fourth exemplary embodiment of the drug delivery device 10 during cap removal.

Here, the grasper 12.1 comprises at least one pair of flexible arms 12.1.1, further continued as grasper arms 12.1.1, biased outwards. The grasper 12.1 may have one or more than two grasper arms 12.1.1 (not shown). For example, several grasper arms 12.1.1 are symmetrically distributed around the entire circumference of the grasper 12.1.

During final assembly, the grasper arms 12.1.1 are deflected inwards by a certain assembly tool and are maintained in this position when the cap 12 is placed onto the drug delivery device 10 by an inner circumference of the needle shroud 13. While removing the cap 12 before use of the device 10, the grasper arms 12.1.1 relaxes outwards in a gap 12.4 within the cap 12 after passing the distal end of the needle shroud 13. Due to the outwardly biased grasper arms 12.1.1, the cap 12 cannot be replaced onto the drug delivery device 10 without the certain assembly tool. Thus, a replacement of the cap 12 after use of the drug delivery device 10 is prevented.

Figure 12:
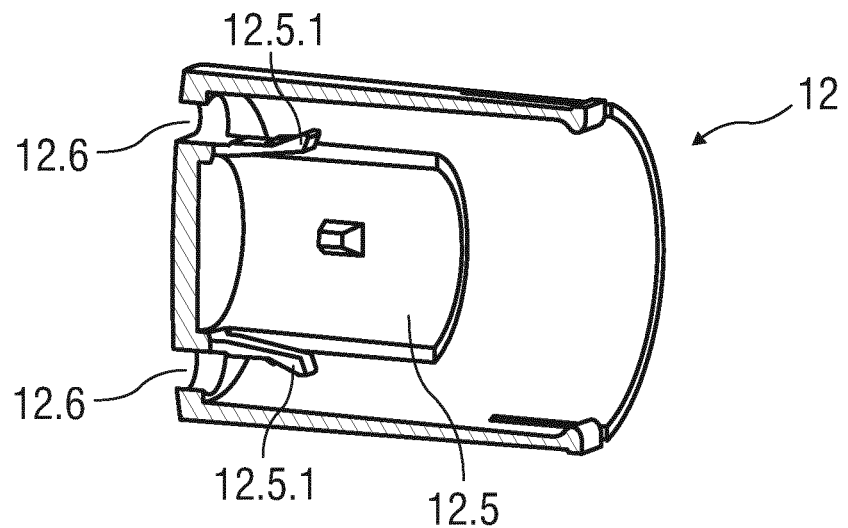
FIG. 12 is a perspective cut-out view of a cap of a fifth exemplary embodiment of a drug delivery device.

FIG. 12 shows a perspective cut-out view of the cap 12 of a fifth exemplary embodiment of a drug delivery device 10.

In the fifth embodiment, the cap 12 comprises at least one pair of flexible arms 12.5.1, further continued as cap arms 12.5.1, that are biased outwardly and that are arranged on an inner cap tube 12.5. The cap arms 12.5.1 have the same function as the grasper arms 12.1.1. The cap arms 12.5.1 are deflected inwards during final assembly by a certain assembly tool and are maintained in this position when the cap 12 is placed onto the drug delivery device 10 by an inner circumference of the needle shroud 13. While removing the cap 12 before use of the device 10, the cap arms 12.5.1 relaxes outwards in the gap 12.4 within the cap 12 after passing the distal end of the needle shroud 13. Due to the outwardly biased cap arms 12.5.1, the cap 12 cannot be replaced onto the drug delivery device 10 without the certain assembly tool. Thus, a replacement of the cap 12 after use of the drug delivery device 10 is prevented nearly similar to the fourth exemplary embodiment of the drug delivery device 10. Furthermore, the cap arms 12.5.1 provide a stable control subassembly state, because the cap arms 12.5.1 can only deflected inwards during final assembly by the certain assembly tool. Therefore, the post-use shroud lock L2 is protected before final assembly (see FIG. 14).

Figure 13:
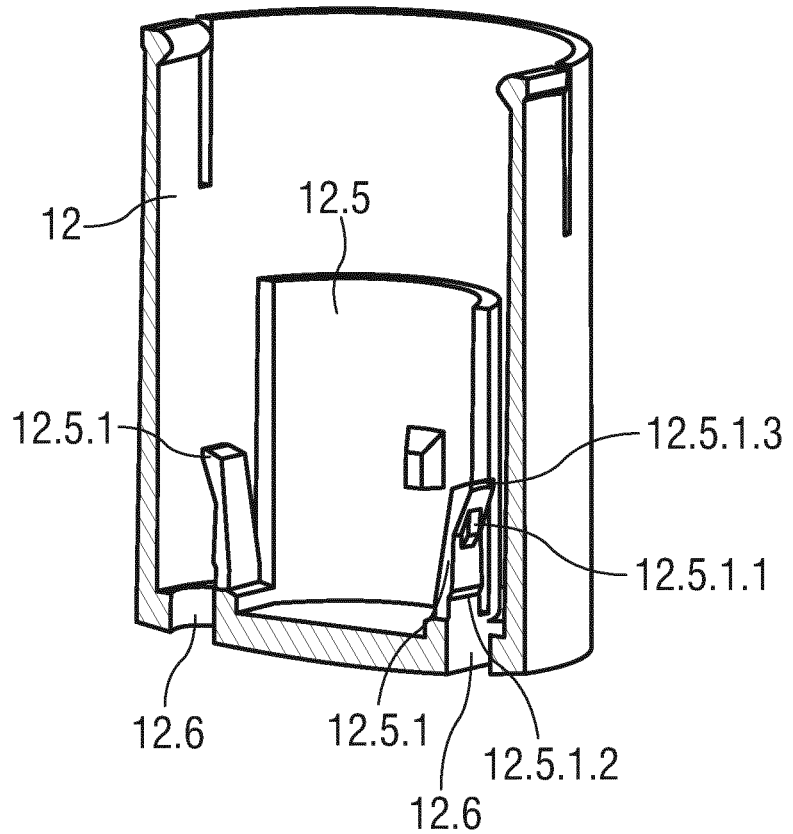
FIG. 13 is a further perspective cut-out view of the cap of a drug delivery device according to the fifth exemplary embodiment.

FIG. 13 shows a further perspective cut-out view of the cap 12 according to the fifth exemplary embodiment of the drug delivery device 10. The cap arms 12.5.1 are shown in more detail.

The cap arms 12.5.1 respectively comprise a ramped rib 12.5.1.1, a thinned region 12.5.1.2 proximally from the ramped rib 12.5.1.1 and a barb profile 12.5.1.3 arranged on a free end of the cap arms 12.5.1. The ramped rib 12.5.1.1 is provided to allow deflecting the cap arm 12.5.1 inwards during final assembly of the control sub-assembly 10.1. The thinned region 12.5.1.2 is provided to define the bending, which acts in the thinned region 12.5.1.2. The barb profile 12.5.1.3 prevents recapping of the drug delivery device 10 after using it.

Figure 14:
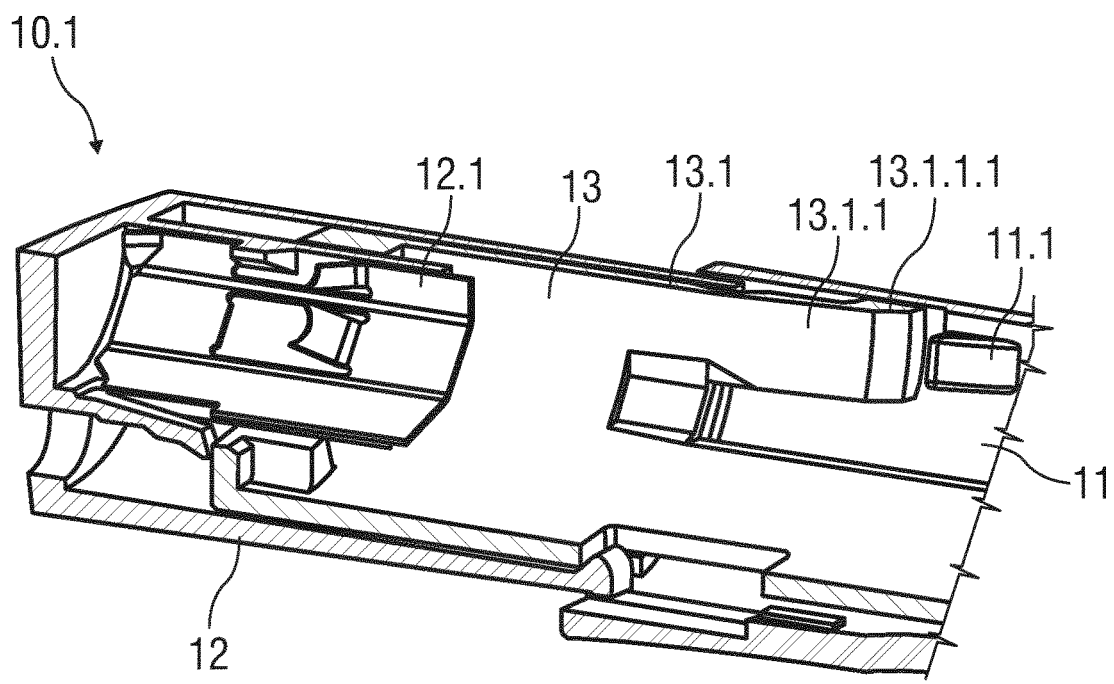
FIG. 14 is a perspective cut-out view of a control-subassembly of a drug delivery device according to the fifth exemplary embodiment.

FIG. 14 shows a perspective cut-out view of the control-subassembly 10.1 of the drug delivery device 10 according to the fifth exemplary embodiment.

The free end of each cap arm 12.5.1 distally abuts the distal end of the needle shroud 13 during the control-subassembly state so the cap 12 is not allowed for proximal movement with respect to the needle shroud 13. Thus, the cap arms 12.5.1 maintain in the relaxed position during control-subassembly state and are in an unstressed position. Creep may be avoided during storage of the control-subassembly 10.1.

Figure 15:
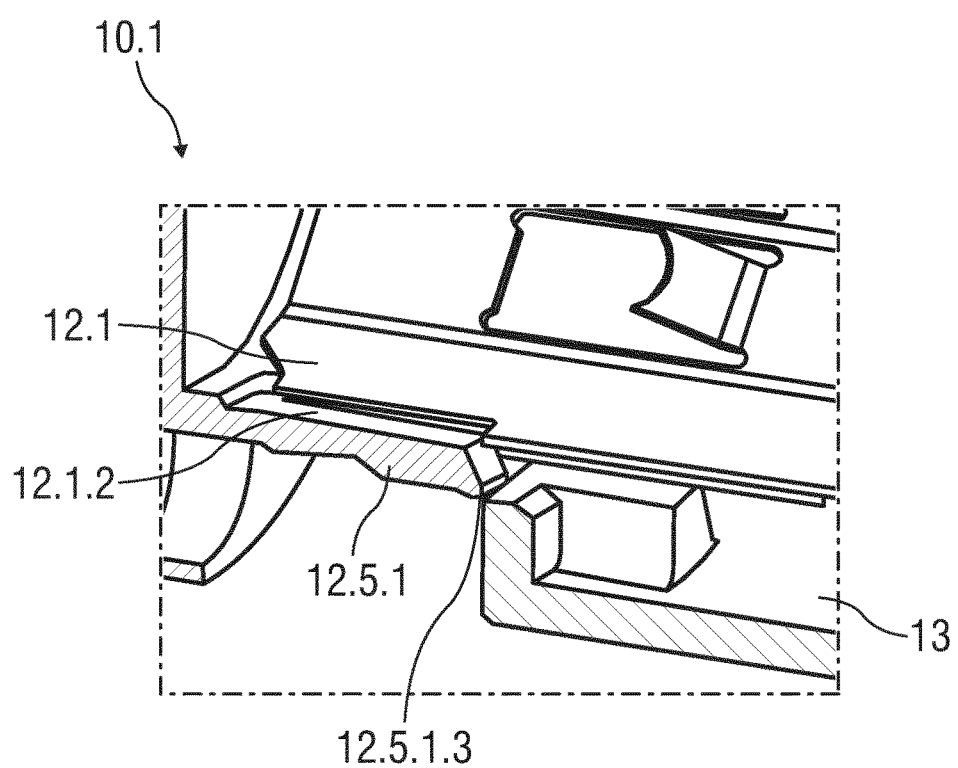
FIG. 15 is an enlarged perspective cut-out view of the control-subassembly of a drug delivery device according to the fifth exemplary embodiment during assembly.

FIG. 15 shows an enlarged perspective cut-out view of the control-subassembly 10.1 according to the fifth exemplary embodiment of the drug delivery device 10 during final assembly.

The cap arms 12.5.1 are deflected inwardly by the not shown assembling tool, e. g. a pin that is inserted through priming holes 12.6 (see FIGS. 11 to 13). This allows the cap arms 12.5.1 to move within the needle shroud 13, thereby overcoming the distal end of the needle shroud 13 with the barb profile 12.5.1.3 so the cap 12 may be fully placed onto the drug delivery device 10. To provide clearance required to allow the cap arms 12.5.1 to deflect inwards, the grasper 12.1 may comprise a number of slots 12.1.2 (shown in FIG. 18 in more detail).

During assembly, the cap arms 12.5.1 deflect inwards when passing the distal end of the needle shroud 13. After passing the distal end of the needle shroud 13, the cap arms 12.5.1 relax into a shroud gap 13.1.3 (shown in FIG. 17) that is arranged on a distal end of the needle shroud 13. The shroud gap 13.1.3 is formed by an increased inner diameter of the distal end of the needle shroud 13.

Figure 16:
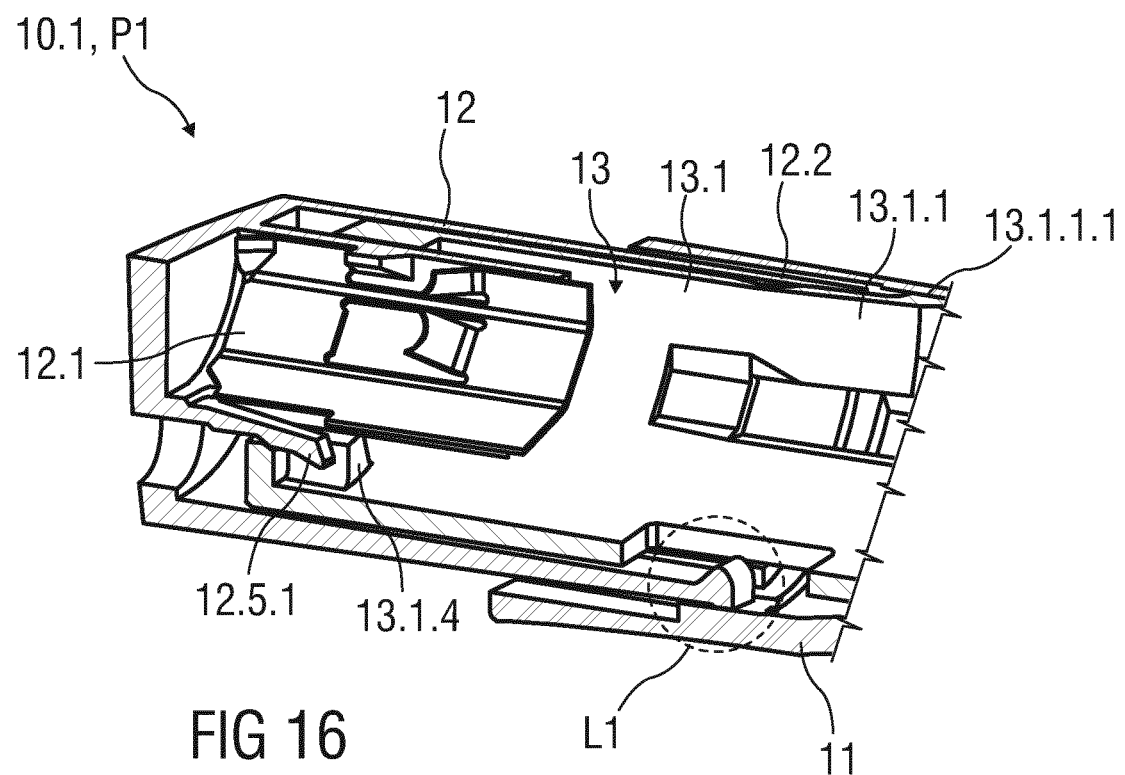
FIG. 16 is a perspective cut-out view of a control-subassembly of a drug delivery device according to the fifth exemplary embodiment after assembly in a pre-use state.

FIG. 16 shows a perspective cut-out view of the control-subassembly 10.1 of the drug delivery device 10 according to the fifth exemplary embodiment after assembly in the pre-use state P1.

The cap arms 12.5.1 are inserted into the needle shroud 13 and in a relaxed state due to the shroud gaps 13.1.3. This prevents relaxation of the cap arms 12.5.1 due to creep.

The needle shroud 13 further comprises a number of inner ribs 13.1.4 arranged on the distal end and protruding radially inwards. The inner ribs 13.1.4 are provided to prevent the shroud spring 13.2 from joining the cap arms 12.5.1. In particular, the inner ribs 13.1.4 offset the shroud spring 13.2 from the distal end of the needle shroud 13.

Figure 17:
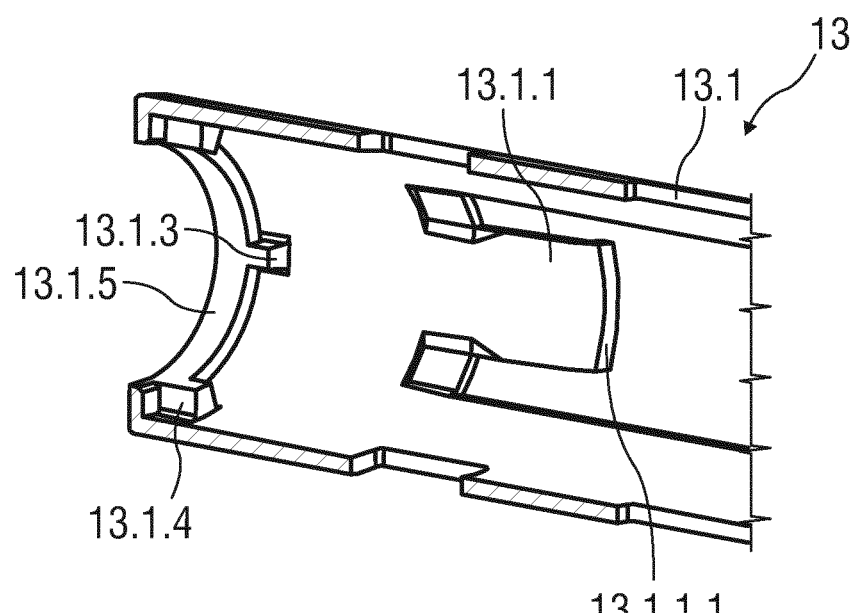
FIG. 17 is a perspective view of a needle shroud of a drug delivery device according to the fifth exemplary embodiment and FIG. 18 is a perspective view of a grasper of a drug delivery device according to the fifth exemplary embodiment.

FIG. 17 shows a perspective view of the needle shroud 13 of the drug delivery device 10 according to the fifth exemplary embodiment.

The needle shroud 13 is shown separately so the shroud gap 13.1.3 and the inner ribs 13.1.4 can be viewed in more detail. The distal end of the needle shroud 13 comprises an inner wall reinforcement 13.1.5 projecting radially inwards. The inner ribs 13.1.4 are arranged proximally from the reinforcement 13.1.5 and may be formed integrally with the reinforcement 13.1.5. The shroud gaps 13.1.3 are configured as interruptions of the reinforcement 13.1.5.

Figure 18:
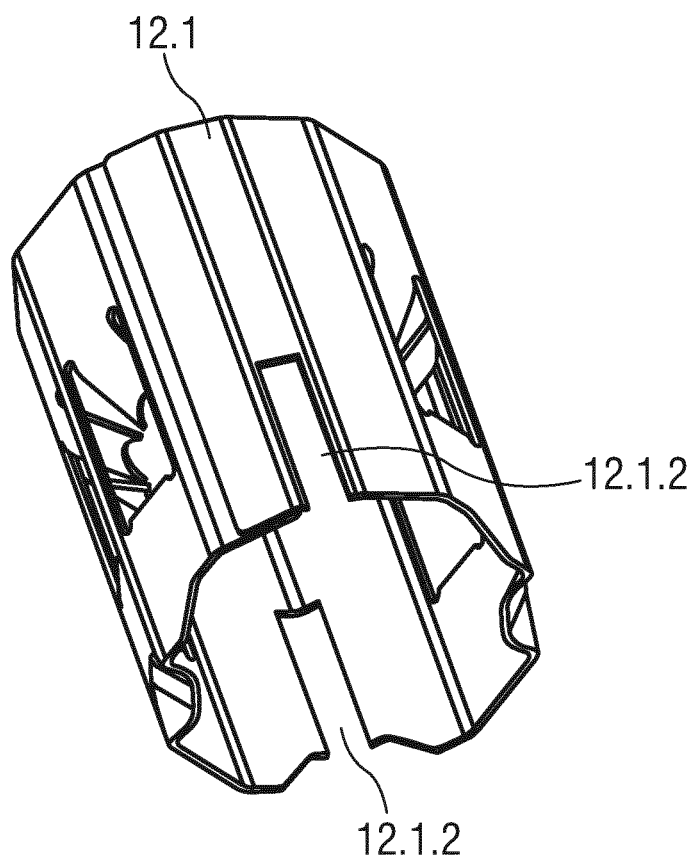

FIG. 18 shows a perspective view of the grasper 12.1.1 of the drug delivery device 10 according to the fifth exemplary embodiment.

The grasper 12.1.1 is shown separately so the number of slots 12.1.2 (here two slots 12.1.2) can be viewed in more detail. The slots 12.1.2 increase the clearance for the cap arms 12.5.1 once they are deflected. This prevents an increase of a cap removal force, because the cap arms 12.5.1 do not join the grasper 12.1. Instead of the slots 12.1.2, a length of the cap arms 12.5.1 may be increased.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

LIST OF REFERENCES 10 drug delivery device
10.1 control-subassembly
11 housing
11.1 housing ramp
11.2 locking pin
11a window
12 cap assembly
12.1 grasper
12.1.1 grasper arm
12.1.2 slot
12.2 proximal cap end
12.3 cut-out
12.4 gap
12.5 inner cap tube
12.5.1 cap arms
12.5.1.1 ramped rib
12.5.1.2 thinned region
12.5.1.3 barb profile
12.6 priming hole
13 needle shroud
13.1 shroud body
13.1.1 shroud beam
13.1.1.1 locking tab
13.1.1.2 shroud ramp
13.1.1.3 recess
13.1.2 projection
13.1.3 shroud gap
13.1.4 inner rib
13.1.5 reinforcement
13.2 shroud spring
13.3 projection
16 syringe carrier
16.1 locking pin
17 needle
20 distal region of the drug delivery device
21 proximal region of the drug delivery device
22 button
23 piston
24 cartridge
30 energy source, e.g. drive spring
40 plunger
E steep edge
L1 pre-use shroud lock
L2 post-use shroud lock
P1 pre-use state
P2 post-use state

The invention claimed is:

1. A drug delivery device comprising:
a housing configured to contain a drug container with a needle;
a needle shroud that is telescopically coupled to the housing; and
a cap that is configured to be releasably connected to the housing before use of the drug delivery device,
wherein at least one of the cap and the needle shroud is configured to at least partially prevent the cap from being reapplied onto the housing after use of the device, and wherein the needle shroud comprises a shroud beam that is biased radially outwards from a shroud body, the shroud beam has a locking tab protruding outwards and the locking tab comprises a distal steep edge configured as a distal stop for a proximal cap end when the cap is being reapplied onto the housing after use of the device.

2. The drug delivery device of claim 1, wherein:
the cap comprises a grasper having at least one pair of flexible grasper arms that are arranged on a grasper body and that are biased outwards; and
the grasper arms are configured to flex outwards during cap removal.

3. The drug delivery device of claim 1, wherein:
the cap comprises cap arms that are arranged on an inner circumference of the cap and that are biased outwards; and
the cap arms are configured to flex outwards during cap removal.

4. The drug delivery device of claim 3, wherein:
the cap comprises a grasper comprising slots; and
the slots are configured to provide a clearance for the cap arms when the cap arms are deflected.

5. The drug delivery device of claim 3, wherein the needle shroud further comprises shroud gaps configured to receive the cap arms before final assembly of the drug delivery device.

6. The drug delivery device of claim 3, wherein:
the needle shroud comprises inner ribs projecting radially inwards; and
the inner ribs are configured to prevent the cap arms from being joined by a shroud spring.

7. A drug delivery device comprising:
a housing configured to contain a drug container with a needle;
a needle shroud that is telescopically coupled to the housing; and
a cap that is configured to be releasably connected to the housing before use of the drug delivery device, wherein the cap comprises cap arms and a grasper comprising slots, the cap arms being arranged on an inner circumference of the cap, being biased outwards and being configured to flex outwards during cap removal, the slots being configured to provide a clearance for the cap arms when the cap arms are deflected and wherein at least one of the cap and the needle shroud is configured to at least partially prevent the cap from being reapplied onto the housing after use of the drug delivery device.

8. The drug delivery device of claim 7, wherein the needle shroud comprises a shroud beam that is biased radially outwards from a shroud body, the shroud beam comprising a locking tab protruding outwards.

9. The drug delivery device of claim 8, wherein the locking tab comprises a distal steep edge configured as a distal stop for a proximal cap end when the cap is being reapplied onto the housing after use of the drug delivery device.

10. The drug delivery device of claim 7, wherein the needle shroud further comprises shroud gaps configured to receive the cap arms before final assembly of the drug delivery device.

11. A drug delivery device comprising:
a housing configured to contain a drug container with a needle;
a needle shroud that is telescopically coupled to the housing; and
a cap that is configured to be releasably connected to the housing before use of the drug delivery device, wherein the cap comprises cap arms that are arranged on an inner circumference of the cap and that are biased outwards and the cap arms are configured to flex outwards during cap removal, wherein the needle shroud further comprises shroud gaps configured to receive the cap arms before final assembly of the drug delivery device and wherein at least one of the cap and the needle shroud is configured to at least partially prevent the cap from being reapplied onto the housing after use of the drug delivery device.

12. The drug delivery device of claim 11, wherein the needle shroud comprises a shroud beam that is biased radially outwards from a shroud body, the shroud beam comprising a locking tab protruding outwards.

13. The drug delivery device of claim 12, wherein the locking tab comprises a distal steep edge configured as a distal stop for a proximal cap end when the cap is being reapplied onto the housing after use of the drug delivery device.

14. The drug delivery device of claim 11, wherein the needle shroud comprises inner ribs projecting radially inwards and the inner ribs are configured to prevent the cap arms from being joined by a shroud spring.

* * * * *